US006183774B1

(12) United States Patent
Aust et al.

(10) Patent No.: US 6,183,774 B1
(45) Date of Patent: *Feb. 6, 2001

(54) STABILIZING VITAMIN A DERIVATIVES BY ENCAPSULATION IN LIPID VESICLES FORMED WITH ALKYLAMMONIUM FATTY ACID SALTS

(75) Inventors: Duncan T. Aust, Ridge; Michael A. Ross, Jericho; James M. Wilmott, Shoreham; James A. Hayward, Stony Brook, all of NY (US)

(73) Assignee: Collaborative Laboratories, Inc., East Setauket, NY (US)

( * ) Notice: Under 35 U.S.C. 154(b), the term of this patent shall be extended for 0 days.

This patent is subject to a terminal disclaimer.

(21) Appl. No.: 09/375,683

(22) Filed: Aug. 17, 1999

Related U.S. Application Data

(63) Continuation-in-part of application No. 09/255,160, filed on Feb. 22, 1999, now Pat. No. 6,071,535, which is a continuation-in-part of application No. 08/594,175, filed on Jan. 31, 1996, now Pat. No. 5,874,105.

(51) Int. Cl.[7] .............................. A61K 9/127; A61K 7/00
(52) U.S. Cl. .......................... 424/450; 424/401; 264/4.1; 264/4.3; 514/724; 514/725
(58) Field of Search ..................................... 424/450, 401; 264/4.1, 4.3; 436/829; 426/1.21, 9.321, 9.51, 417, 94.3; 516/724, 725

(56) References Cited

U.S. PATENT DOCUMENTS

| | | |
|---|---|---|
| 2,650,165 | 8/1953 | Wahl . |
| 3,957,971 | 5/1976 | Oleniacz . |
| 4,016,100 | 4/1977 | Suzuki et al. . |
| 4,032,663 | 6/1977 | Kobayashi et al. . |

(List continued on next page.)

FOREIGN PATENT DOCUMENTS

| | | |
|---|---|---|
| 0 158 441 A2 | 10/1985 | (EP) . |
| 57-82311 | 11/1980 | (JP) . |
| 0 561 424 B1 | 3/1997 | (JP) . |
| WO 93/19743 | 11/1992 | (WO) . |
| WO 96/31194 | 10/1996 | (WO) . |

OTHER PUBLICATIONS

Hargreaves, W.R. et al., *Monoalkyl Liposomes* 17(18):3759, 1978.

Kaler, E.W. et al., *Science* 245:1371, Sep. 22, 1989.

Vahlquist, A. et al. *J. Invest. Dermatol.*, vol. 94, Holland D.B. and Cunliffe, W.J. (1990), pp. 496–.

Ellis, C.N. et al., *Pharmacology of Retinols in Skin*, vol. 3(1989), pp. 249–252.

Lowe, N.J. et al., *Pharmacology of Retinols in Skin*, vol. 3, (1989), pp. 240–248.

Primary Examiner—Gollamudi S. Kishore
(74) Attorney, Agent, or Firm—Darby & Darby (57) ABSTRACT

The present invention provides for vitamin A derivative selected from the group consisting of retinol, retinyl ester and any combination thereof incorporated into liposomes formed with alkylammonium fatty acid salts, and methods for manufacturing same. The liposomes of the invention may deliver vitamin A derivative materials at the occurrence of a preset triggering condition. Preferred liposomes of the invention are cationic liposomes. The preferred liposomes of the invention are formed with alkylammonium fatty acid salts, e.g., trialkylammonium fatty acid salts of long chain amides. The encapsulated vitamin A derivative is thus stabilized by the liposomes. The present invention thus also provides a method of stabilizing vitamin A derivative be encapsulation in such liposomes. The liposomes of the invention are used to provide topical skin treatment formulations useful in the treatment of skin.

21 Claims, 7 Drawing Sheets

U.S. PATENT DOCUMENTS

| | | |
|---|---|---|
| 4,217,344 | 8/1980 | Vanlerberghe et al. . |
| 4,235,871 | 11/1980 | Papahadjopoulos et al. . |
| 4,247,411 | 1/1981 | Vanlerberghe et al. . |
| 4,342,826 | 8/1982 | Cole . |
| 4,483,921 | 11/1984 | Cole . |
| 4,485,054 | 11/1984 | Mezei et al. . |
| 4,533,254 | 8/1985 | Cook et al. . |
| 4,619,794 | 10/1986 | Hauser . |
| 4,663,167 | 5/1987 | Lopez-Berestein et al. . |
| 4,708,861 | 11/1987 | Popescu et al. . |
| 4,721,612 | 1/1988 | Janoff et al. . |
| 4,761,288 | 8/1988 | Mezei . |
| 4,812,312 | 3/1989 | Lopez-Berestein et al. . |
| 4,857,319 | 8/1989 | Crowe et al. . |
| 4,873,088 | 10/1989 | Mayhew et al. . |
| 4,888,288 | 12/1989 | Wagner . |
| 4,897,269 | 1/1990 | Mezei . |
| 4,908,154 | 3/1990 | Cook et al. . |
| 4,911,928 | 3/1990 | Wallach . |
| 4,978,654 | 12/1990 | Lopez-Berestein et al. . |
| 5,000,958 | 3/1991 | Fountain et al. . |
| 5,032,457 | 7/1991 | Wallach . |
| 5,128,139 | 7/1992 | Brown et al. . |
| 5,164,182 | 11/1992 | Meybeck et al. . |
| 5,165,994 | 11/1992 | Kaler et al. . |
| 5,190,764 | 3/1993 | Chiba et al. . |
| 5,192,544 | 3/1993 | Grollier et al. . |
| 5,262,310 | 11/1993 | Karube et al. . |
| 5,277,913 | 1/1994 | Thompson et al. . |
| 5,296,231 | 3/1994 | Yarosh . |
| 5,366,881 | 11/1994 | Singh et al. . |
| 5,443,839 | 8/1995 | Meybeck . |
| 5,466,467 | 11/1995 | Singh . |
| 5,585,109 | 12/1996 | Hayward et al. . |
| 5,679,374 | 10/1997 | Fanchon et al. . |
| 5,738,858 | 4/1998 | Burger . |
| 5,744,148 | 4/1998 | Habif et al. . |
| 5,756,109 | 5/1998 | Burger et al. . |
| 5,759,556 | 6/1998 | Burger et al. . |
| 5,874,105 * | 2/1999 | Watkins .............................. 424/450 |

* cited by examiner

● Retinol IOS Catesomes   ■ Retinol IOCM Catesomes
▲ Retinol IOS   □ Retinol IOCM

- ● Retinol IOS Catesomes
- ■ Retinol IOCM Catesomes
- ▲ Retinol IOS
- □ Retinol IOCM

STABILIZING VITAMIN A DERIVATIVES BY ENCAPSULATION IN LIPID VESICLES FORMED WITH ALKYLAMMONIUM FATTY ACID SALTS This is a continuation-in-part of application Ser. No. 09/255,160, filed Feb. 22, 1999 now U.S. Pat. No. 6,071,535 which is a continuation-in-part of application Ser. No. 08/594,175 filed Jan. 31, 1996 (now U.S. Pat. No. 5,874, 105. Each of these prior applications is hereby incorporated herein by reference, in its entirety.

FIELD OF THE INVENTION

The present invention relates to the stabilization of vitamin A derivatives by encapsulation in lipid vesicles formed with long chain alkylammonium fatty acid salts. The present invention also relates to compositions comprising such liposomes for the cosmetic or dermatological treatment of imperfections or complaints of the skin, including the scalp. More particularly, the invention relates to a composition for treating the skin comprising at least one vitamin A derivative as an active agent encapsulated in the long chain alkylammonium fatty acid salt liposomes of the invention and methods of using such compositions.

BACKGROUND OF THE INVENTION

Liposome formation is a natural result of the amphipathic nature of the molecules of which they are comprised. Amphipathic molecules are those molecules with distinct regions of the molecule having hydrophilic character and distinct regions of the same molecule having hydrophobic character. When dispersed in water, amphipathic molecules form three types of macro-molecular structure: micelles, hexagonal phase and lipid bilayers. The exact macromolecular structure which is formed depends on the relative sizes of the hydrophilic and hydrophobic regions of the molecule.

Figure 1:
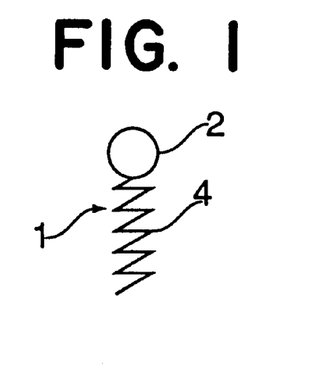
FIG. 1 is a pictorial representation of a detergent molecule.
Figure 2:
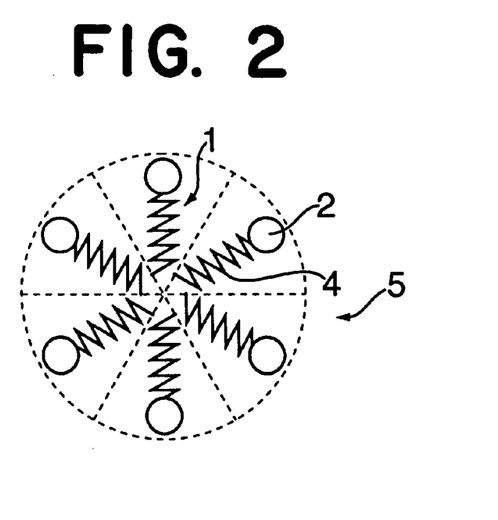
FIG. 2 is a pictorial representation of a micelle structure formed of a detergent molecule such as that represented in FIG. 1.

Micelle formation is favored when the cross sectional area of the hydrophilic region of the molecule is greater than that of the hydrophobic part of the molecule. Detergents are examples of such molecules, e.g., sodium palmitate. Detergents contain a hydrocarbon chain (the hydrophobic portion of the molecule) and an ionic base (the hydrophilic portion of the molecule), and act as emulsifying agents to bind water and oil phases. That is, detergents allow oil and water to be broken into tiny droplets suspended or dispersed in water. Particular detergents 1 may be classified as anions (negatively charged at the hydrophilic portion) and may be represented, as shown in FIG. 1, as having a hydrophilic head 2 with a hydrocarbon (hydrophobic) tail 4. FIG. 2 is a representation of a micelle structure 5 formed of a number of detergent molecules due to their hydrophilic/hydrophobic character.

Figure 4:
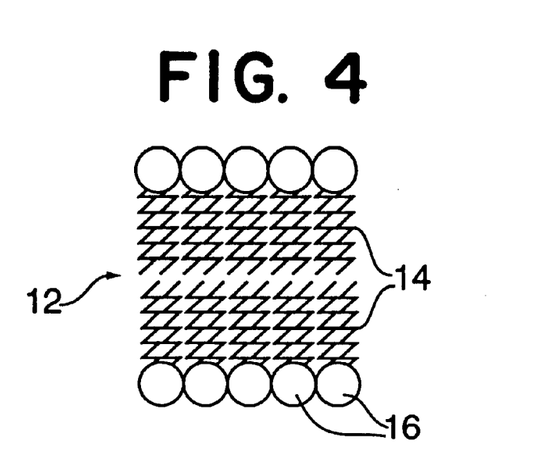
FIG. 4 is a pictorial representation of a phospholipid bilayer.
Figure 4A:
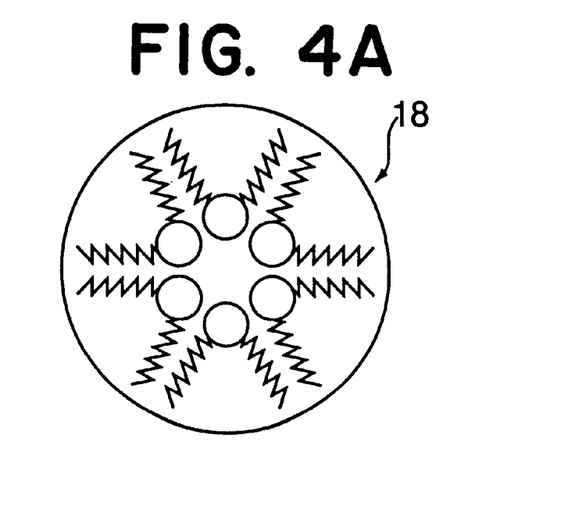
FIG. 4A is a pictorial representation of an inverted micelle.

In the opposite conformation, i.e., when the cross sectional area of the hydrophobic region of the molecule is greater than that of the hydrophilic part of the molecule, the formation of hexagonal phase structures is favored, e.g., dimyristoyl-phosphatidylethanolamine (DMPE). FIG. 4A is a representation of a hexagonal phase structure, sometimes referred to as an inverse micelle.

Figure 3:
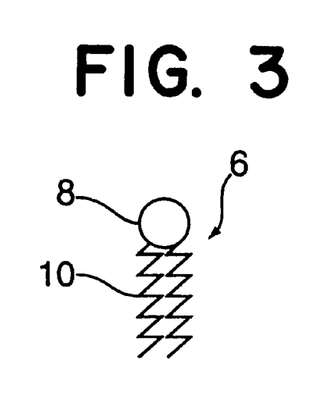
FIG. 3 is a pictorial representation of a phospholipid molecule.

For molecules in which the cross sectional area of the hydrophilic region of the molecule is slightly less than, or equal to, that of the hydrophobic part of the molecule, such as many phospholipids, the formation of bilayers is favored, e.g., dipalmitoylphosphatidylcholine (DPPC). Phospholipids are an amphipathic type of lipid which contain phosphate, that is, molecules containing one phosphate, a glycerol and one or more fatty acids. FIG. 3 is a simplified representation of a phospholipid molecule 6, including a hydrophilic head 8 (i.e., the phosphate and glycerol) and a hydrophobic tail 10 (i.e., the one or more fatty acids). FIG. 4 is a representation of a phospholipid bylayer 12, where the hydrophobic regions 14 of the phospholipid molecules are caused to turn inward due to the aqueous environment, and the hydrophilic portions 16 face outward. These bilayers are two dimensional sheets in which all of the hydrophobic portions, e.g., acyl side chains, are shielded from interaction with water except those at the ends of the sheet. An energetically unfavorable interaction of the acyl chains with water results in the folding of the bilayers to form three-dimensional, vesicles. These vesicles are referred to as "liposomes".

Liposomes may be formed as a single bilayer enclosing a single aqueous space (small unilamellar vesicles; SUVS) or may be composed of concentric bilayers with many aqueous spaces alternating with the bilayers (multilamellar vesicles; MLVS). Liposomes can be used to encapsulate both hydrophobic and hydrophilic materials. Hydrophobic payloads are typically partitioned within the bilayers whereas hydrophilic payloads are typically trapped within the aqueous compartments. The advantages of using liposomes as a carrier/encapsulation system is that they are stable and can protect their payload from degradation, e.g., by oxygen, digestive enzymes, etc.

For example, U.S. Pat. No. 3,957,971, issued May 15, 1976, discloses liposome-formed moisturizing units which are capable of moisturizing and improving flexibility, plasticity, and softness of keratinous matter, particularly mammalian skin. The liposomes within which the moisturizer is stored include a matrix of a ternary lipid mixture of lecithin, dicetyl phosphate, and a sterol, and include cavities disposed within the liposome. The cavities (lamellar space) contain an humectant, such as sodium pyroglutamate, in an aqueous medium. Moisturizing liposomes are also disclosed therein which function osmotically, serving as traps for water, which may be shared with the keratin constituents as required.

Liposomes also may be used for the timed delivery of a wide variety of materials including pharmaceuticals, cosmetics and nutrients. For example, U.S. Pat. No. 4,016,100, issued Apr. 5, 1977, discloses a method of producing a pharmaceutical composition comprised of an aqueous suspension of an active agent entrapped in a spherule of a phospholipid (liposome) The composition, or drug delivery vehicle, is prepared by dispersing a phospholipid uniformly in water to give an aqueous phospholipid dispersion, adding a medicament to the aqueous dispersion and freezing the thus-obtained aqueous dispersion to entrap the medicament in lipid spherules formed. The frozen dispersion is then thawed to realize an aqueous suspension of spherules having diameters of less than 5.0 microns. The timed release of an active agent is directly related to the amount of active agent trapped in the liposomes. The greater the amount of active agent, the longer the release process lasts.

A goal of the liposome research has been the development of a liposomal delivery system that would deliver its payload not over time as in the '100 patent mentioned above, but on cue, i.e., a controlled release, for example, in a mammalian body. For example, a delivery system that delivers its payload when applied to the skin or when arriving at a tumor. A bulk of the research has been based on admixtures of liposomes and other biological macromolecules such as antibodies and lecithins. Various degrees of success have been achieved with these systems but none have produced a liposome that will release its payload, or not, depending on the prevailing conditions. The invention described herein is just such a liposome: the degree of, payload encapsulation may be altered by changes in pH and/or ionic strength of the surrounding medium thereby realizing a triggered delivery system in a form of a liposome.

Vitamin A derivatives are desirable ingredients in cosmetic formulations. Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g., Vahlquist, A. et al., J. Invest. Dermatol., Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N.J. et al., "Pharmacology of Retinols in Skin", Vol. 3, (1989), pp. 240–248; PCT Patent Application No. WO 93/19743.

It is believed that the use of retinol and retinyl esters would be preferred over the use of retinoic acid in the treatment of skin due to the fact that retinol is both an endogenous compound found in the body and are considered much safer than retinoic acid.

Retinol and retinyl esters are known for their beneficial effects on the skin, in particular in topical application. Retinol and retinyl esters have for a long time been used in the treatment of acne. However, it is in the field of repair of damage caused either by age or by over-exposure to the sun that retinol has proven to be extremely active. Thus, the effects of retinol retinyl esters on cell differentiation make it possible to envisage their use thereof for effectively combating the appearance of wrinkles and fine lines, and for combating dryness, roughness and/or stiffness of the skin. In addition, they are active as antioxidants in the regeneration of tissues. Repeated application of cosmetic compositions containing retinol and/or retinyl esters have enabled wrinkles to be removed, the skin to be rendered smooth and small cracks in the epidermis to be repaired.

On account of these beneficial effects, it has for a very long time been sought to formulate retinol and retinyl esters in cosmetically acceptable compositions in a form which is stable over time at room temperature. However, retinol and retinyl esters have been shown to be unstable when stored over time and are thus difficult to formulate into cosmetic compositions. Particularly, retinol and retinyl esters are highly sensitive to elevated temperatures and result in significant color changes upon degradation.

Thus, although retinol and retinyl esters are considered safer to use than retinoic acid, they are less effective than retinoic acid at providing skin benefits due to their decreased stability which leads to inactivation. It would thus be highly desirable to stabilize the unstable vitamin A derivatives, retinol and/or retinyl esters, for use in the treatment of skin.

A number of methods have been adopted to stabilize the breakdown of vitamin A.

U.S. Pat. No. 5,738,858 discloses skin care compositions containing fatty hydroxyethyl imidazoline surfactants in combination with retinol and/or retinyl esters for use in stabilizing such compounds.

U.S. Pat. No. 5,756,109 discloses skin care compositions containing geranyl geraniol in combination with retinol and/or retinyl esters for use in stabilizing such compounds.

U.S. Pat. No. 5,759,556 discloses skin care compositions containing cyclic aliphatic unsaturated aldehydes, ketones alcohols or esters in combination with retinol and/or retinyl esters for use in stabilizing such compounds.

U.S. Pat. No. 5,744,148 discloses skin care compositions containing emulsions of unstable retinol and/or retinyl esters in an oil phase for use in stabilizing such compounds.

Encapsulation of retinol into liposomes has also been shown to be effective in enhancing the stability of the encapsulated vitamin A derivatives, however, none of these liposomes incorporate the preferred cationic long chain alkylammonium fatty acid salt liposomes of the invention.

U.S. Pat. No. 5,679,374 discloses the encapsulation of retinol into two different types of liposome compositions which allow for the simultaneous action of two different active agents, one of which may be retinol and its derivatives. The different liposomes used provide for penetration into different areas of the skin, i.e. surface layers and deep layers. The liposomes used are not cationic liposomes and there is no enhancement of the stability of the retinol is shown.

WO 96/31194 discloses the encapsulation of retinoids into non-phospholipid, non-ionic liposomes which provide for increased chemical stability over a long period of time. However, the liposomes used are non-ionic and do not display the characteristics of the cationic liposomes of the invention.

U.S. Pat. No. 5,192,544 discloses the encapsulation of a retinoid compound into phospholipid liposomes with the concomitant incorporation of a pyrimidine derivative which is used to enhance stabilization.

It has now surprisingly been found that unstable vitamin A derivatives, when encapsulated in liposomes formulated with long chain alkylammonium fatty acid salts as described in U.S. Pat. No. 5,874,105, issued Feb. 23, 1999, show a significant improvement in long term stability.

SUMMARY OF THE INVENTION

It is an object of the present invention to provide a composition comprising liposome encapsulated vitamin A derivative or derivatives which enhances the stability of the vitamin A derivative or derivatives encapsulated therein.

The liposome composition of the invention is formed with long chain alkylammonium fatty acid salts as described in the above-identified U.S. Pat. No. 5,874,105 which is hereby incorporated herein by reference in its entirety.

The long chain alkylammonium fatty acid salt liposomes used to encapsulate the vitamin A derivative or derivatives deliver their entrapped load at the occurrence of a preset condition and display cationic characteristics. The liposomes are formed with trialkylammonium fatty acid salts, of long chain amides such that a portion of the molecular structure defined thereby includes a portion which readily adheres to protein and like molecules. Such liposomes are capable of delivering their load upon the occurrence of a trigger or control condition. It has surprisingly been found that the encapsulation of vitamin A derivatives in such liposome compositions provides for enhanced stability of the encapsulated vitamin A derivative or derivatives at various temperatures over time.

Upon being passed from an environment characteristic of a particular pH or temperature, the molecular structure of the long chain alkylammonium fatty acid salt liposomes becomes unstable in the changed environment causing the liposomes to deliver their vitamin A derivative(s) load.

The particular liposomes of the invention which are used to encapsulate the vitamin A derivative or derivatives may be formed in accordance with the process or processes of manufacture disclosed in the above-identified U.S. Pat. No. 5,974,105. An example of such liposomes is marketed under the tradename CATEZOMES™.

It is another object of the invention to provide topical skin treatment formulations in the treatment of skin imperfections, dry skin, photodamaged skin, wrinkles, age spots, acne, skin lightening, psoriasis, and atopic dermatosis It is yet another object of the invention to provide a method for treating the skin comprising administering to the skin a topical skin treatment formulation comprising at least one vitamin A derivative as an active agent encapsulated in the long chain alkylammonium fatty acid salt vesicles of the invention.

DETAILED DESCRIPTION

The liposome compositions of the invention contain, as a first essential ingredient, a vitamin A derivative which is defined herein as a compound or mixture of compounds selected from the group consisting of retinol, retinyl ester or any combination thereof. Retinol and retinyl esters are known to be unstable, yet they are desired ingredients in cosmetic formulations.

As used herein, the term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. As used herein, the term "retinol" has been defined above. Retinyl esters suitable for use in the present invention are C1–C30 esters of retinol, preferably C2–C20 esters, and most preferably C2, C3, and C16 esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, due to their wide commercial availability. Retinyl linoleate ester is also preferred due to its efficacy.

The vitamin A derivative for use in the invention may be admixed with emollients in order to aid in solubilization of the vitamin A derivative. The vitamin A derivative must be fully solubilized in the emollient prior to mixing with the liposome components of the invention. The vitamin A derivative is solubilized with the emollients prior to incorporation into liposomes in a concentration range of from about 0% w/w (vitamin A derivative/emollient) to about 50% w/w. A preferred concentration range is from about 0.1% w/w to about 30% w/w. A particularly preferred concentration range is from about 5.0% w/w to about 20% w/w.

The emollients to be used in the invention may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins. Additional hydrocarbon oils which can be used as emollients include but are not limited to corn, safflower and vegetable oils.

The Vitamin A derivative or Vitamin A derivative/emollient mixture are added to the liposome formulation mixture prior to incorporation into liposomes to give a concentration range of vitamin A derivative in the liposome formulation mixture of from at least about 0.01% w/w to at least about 50% w/w, preferably from at least about 0.1% w/w to at least about 30% w/w, and most preferably from at least about about 1% w/w to about 20% w/w.

The A-ADDA molecules to be used in the formulation of the liposomes of the invention are incorporated into the liposome formulation mixture prior to incorporation into liposomes in a concentration range of from about 0.01% w/w to about 20% w/w. A preferred concentration range is from about 0.1% w/w to about 10% w/w. A particularly preferred concentration range is from about 1% w/w to about 5% w/w.

In a further embodiment, a co-solvent may also be incorporated with the liposomes of the invention. The co-solvent is not required in the liposome formulations of the invention. Such incorporation may be carried out either prior to or following liposome formulation by incorporating the co-solvent either into the liposome formulation mixture or into the liposome formulation after the liposomes have been made. Examples of such co-solvents to be incorporated include but are not limited to propylene glycol, polyethylene glycol butylene glycol or any combination thereof. Examples of preferred polyethylene glycols include PEG 200, PEG 2000, PEG-4 and PEG-8. The co-solvent to be used in the compositions of the invention are incorporated into the liposome formulation mixture or into the liposome formulation in a concentration range of from about 0% w/w to about 50% w/w. A preferred concentration range for the co-solvent is from about 0% w/w to about 10% w/w.

In yet a further embodiment, a germicide may also be incorporated in the liposomes of the invention. The germacide is not required in the liposome formulations of the invention. As with the co-solvent, such incorporation may be carried out either prior to or following liposome formulation by incorporating the germacide either into the liposome formulation mixture or into the liposome formulation after the liposomes have been made. Such germicide acts as a preservative to prevent the growth of bacteria during storage of either the liposomes or formulations incorporating such liposomes. Such germicides are well known in the art of cosmetic formulations. Non-limiting examples of such germicides include Germazide MPB™, Midtect TF-60™, Midpol 2000™, Midpol PHN™, Germall II™, Glydant™, Glydant Plus™, Paragon II™, Myavert C™, Germall 115™, Glycacil-L™, Kathon CG™, Merguard 1190™, Merguard 1200™, Phenonip™, Uniphen P-23™, GermnabenIl™, Germaben II-E™, Dowicil 200™, Suttocide A™ and Irgasan DP-300™. The germacide to be used in the compositions of the invention are incorporated into the liposome formulation mixture or into the liposome formulation in a concentration range of from about 0% w/w to about 10% w/w. A particularly preferred concentration range is from about 0% w/w to about 3% w/w.

All of the components of the liposome formulation mixture are preferably dispersed in water or any suitable buffering solution having a pH of around 5 to 11 and an ionic strength of less than about 1 molar NaCl along with the vitamin A derivative(s), along with any co-solvent or gemacide to be added either before or after liposome formulation.

The processing and formulation of retinol and/or retinyl esters into the liposome compositions described herein provide for a highly stable vitamin A derivative product which is easily formulated into cosmetic bases.

This invention thus relates to the encapsulation of vitamin A derivative in water-insoluble lipid vesicles (liposomes) prepared from alkylammonium fatty acid salts. While liposomes are not new, the liposomes disclosed in the above-identified U.S. Pat. No. 5,874,105, which can be inexpensively and efficiently formed and which display cationic characteristics as well as an ability to deliver their loads at the occurrence of a predetermined triggering condition were heretofore unknown. For example, U.S. Pat. No. 4,721,612, discloses a method and composition for the preparation of conventional lipid vesicles (liposomes) the bilayers of which comprise a salt form of an organic acid derivative of a sterol, such as the tris-salt form of a sterol hemisuccinate. The method disclosed therein allows for liposome formation which may be used to entrap compounds which are insoluble in aqueous solutions, such as bioactive agents of limited solubility. This conventionally formed liposome, however, includes no method for controlling delivery.

In contrast, liposomes used in the present invention, because of their unique construction are highly sensitive to both pH and ionic strength of the surrounding medium in which they reside and are therefore specifically deliverable. This unique property results in part because they are formed of alkylammonium fatty acyl salts which are stabilized by a salt bridge. Such a characteristic provides the method to control the release of the load. The liposomes of the invention deliver their loads at the occurrence of a predetermined triggering condition. Examples of such triggering conditions include drying, heating, increased ionic strength and changes in pH. Preferably, the liposomes of this invention are formed with molecules which consist of the following parts: a fatty acid of between 12 and 28 carbon atoms; an $N_n,N_n$-dimethyl-1,n-diamino alkyl (DDA) chain with the number of carbons (n) being equal to 2–8, for example $N_3,N_3$-dimethyl-propyl-1,3-diamine [$NH_2(CH_2)_3N(CH_3)_2$]; and a fatty acid of between 10 and 30 carbon atoms, together forming the ADDA. To form its basic structure, one molecule of fatty acid is linked via an amide bond to the primary amino group of the DDA to form an acyl-DDA (ADDA), for example, behenyl-DDA or palmitol-DDA. Such ADDA material is available under the trade name Catemol from the Phoenix Chemical Co. of Somerville, New Jersey, i.e., Catemol 220 and 160, respectively.

When the fatty acid is behenic acid ($C_{22}$) and the DDA has 3 carbon atoms, the molecule would be $N_1$-behenamido-$N_2$, $N_2$-dimethyl-propyl-1,3-diamine [$CH_3(CH_2)_{20}CONHCH_2CH_2CH_2N(CH_3)_2$], (BDDP). Phoenix also sells another major group of chemicals which are a mixture of Catemol 220 and behenic acid, or Catemol 160 with palmitic acid to get Catemol 220B and 160P respectively. These are referred to herein as A-ADDAs (B-BDDP and P-PDDP). The ADDAs are cationic due to the quaternary amine; the A-ADDPs are inherently neutral. It should be noted that at pH less than about 10.5, the tertiary amine of the DDA will be protonated to form a quaternary amine with a positive charge. Free fatty acid carboxyl groups, attached to the tertiary amine group via the salt bridge, such as behenyl, have a pK of approximately 5 and so above a pH of 5 will be deprotonated and display a negative charge.

Figure 5:
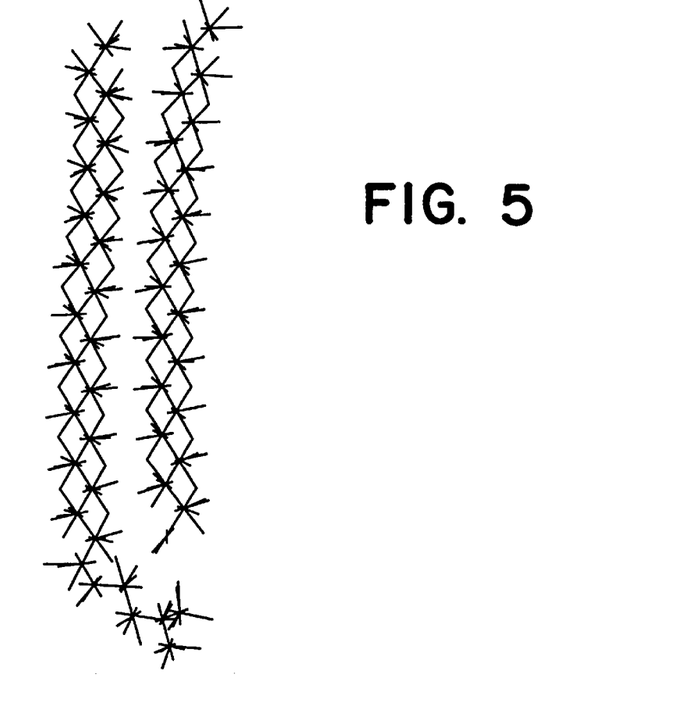
FIG. 5 is an energy minimized molecular model of B-BDDP, produced by a molecular modeling program Insight II on a Silicon Graphics Indigo 4×24 work station.

To form A-ADDAS, the ADDA is mixed with a second fatty acid of between 12 and 28 carbon atoms in equimolar proportions and at a pH between 6 and 10 such that a salt is formed between the quaternary amine group of the ADDA and the carboxyl group of the fatty acid to form acyl ADDA (A-ADDA). An example where the ADDA is BDDP and the first fatty acid is behenic acid (C22) would be behenyl-$N_1$-behenamido-$N_2,N_2$-dimethyl-propyl-1,3-diamine [$CH_3(CH_2)_{20}COO^- \cdot CH_3(CH_2)_{20}CONHCH_2CH_2CH_2N(CH_3)_2$], (B-BDDP). An energy minimized molecular model of B-BDDP is presented in FIG. 5. It is apparent from the molecular model shown in FIG. 5 that these molecules are amphipathic: the salt bond region of the molecule being polar, the alkyl chain region of the molecule being hydrophobic. The molecule is also approximately cylindrical in cross-section and thus would be predicted to form bilayers and liposomes in aqueous media as described above.

The long chain (greater than twelve carbons) A-ADDA is dispersed in a suitable vehicle (water or any aqueous solution having a pH range between 4.5 and 10.5 and an ionic strength of less than, or equivalent to 1 molar NaCl) either by using a mechanical homogenizer at ambient temperature or by stirring at a temperature above that of the melting point of the components of the mixture. Following dispersion of the hydrocarbons in the vehicle, the mixture is subjected to high-sheer processing. The precise conditions for the high-sheer processing step must be established empirically for each mixture.

In this context, high-sheer processing refers to any technique which is capable of mixing ingredients (liquid, solid or mixtures of both) in such a manner that significant energy is imparted to the mixture. Examples would include sonnicators, high-speed mixers and microfluidizers, which are conventional. In particular, U.S. Pat. Nos. 4,533,254 and 4,908,154, disclose conventional methods and apparatus for forming emulsions, a term used to include microemulsions, which could be utilized herein. A sheet within an emulsion-forming liquid mixture is forced under pressure to impinge upon itself in a low-pressure turbulent zone of the liquid utilizing an apparatus comprising a plurality of nozzles with elongated orifices for ejecting, under pressure, sheets of the emulsion-forming liquid. The jets are arranged to effect impingement of the sheets along a common liquid jet interaction front, thereby imposing mechanical energy. Such devices offer great flexibility in choice and amounts of immiscible liquids and emulsifying agents.

Similarly, mixing ADDA with a long chain alcohol (C12, C28), e.g., behenyl alcohol, will also result in a molecule with cylindrical cross-section. In this case, however, the cationic charge of the DDA is not neutralized and the liposomes which are formed have a large cationic surface charge.

The A-ADDA molecules used in the formulation of the liposomes of the invention form bilayers and liposomes which encapsulate the vitamin A derivative(s) of the invention into the bilayer regions.

The liposomes of the invention deliver their loads at the occurrence of a predetermined triggering condition. Examples of such triggering conditions include drying, heating, increased ionic strength and changes in pH. The Catezomes™ liposomes of the invention preferentially deliver and keep their payloads at the stratum corneum of the skin. The liposomes of the invention release their payload slowly over time, thus providing for delivery of the vitamin A derivative(s) over a prolonged period. The increased stabilization of the vitamin A derivative(s) by encapsulation in lipid vesicles formed with alkylammonium fatty acid salts allows for such long term delivery by preserving the vitamin A derivative(s) and protecting them from degradation.

The final liposome products of the invention are comprised of retinol or retinyl ester in a final concentration range of from about 0.001% to about 20%, preferably in an amount of from about 0.01% to about 10%, most preferably in an amount of from about 0.01% to about 5.0%.

Cosmetically Acceptable Vehicle

The composition according to the invention formulated into topical skin treatment formulation by admixing the liposomes of the invention into a cosmetically acceptable vehicle to act as a dilutant, dispersant or carrier for the active components in the composition so as to facilitate their distribution when the composition is applied to the skin.

Vehicles other than water can include liquid or solid emollients, solvents, humectants, thickeners and powders. Especially desirable are mixtures of low and high viscosity silicones. These silicones are available from the General Electric Company under trademarks Vicasil, SE and SF and from the Dow Coming Company under the 200 and 550 Series. Amounts of silicone which can be utilized in the compositions of this invention range anywhere from at least about 5 to at least about 95%, preferably from at least about 25 to at least about 90% by weight of the composition. Gums such as Carbomer™, Natrosol™ and Jaguar™ are additional examples of cosmetic vehicles to be used in the formulation. Additional cosmetic vehicles and methods of formulating cosmetically acceptable topical skin treatment will be well known to those of skill in the art. Examples of such methods may be found in the following references:

Nazarov, T. A. et al., "Study of specific activity of cosmetic creams based on liposomal Compositions", *Vestnik Dermatologii i Venerologii*, No. 5, 48–49, 1994

Burmeister, F. et al., "Liposomes in cosmetic formulations" *Cosmetics & Toiletries* (USA), 111:49–50, 52–53, 1996

Hojerova, J. et al., "Transport systems of biologically active substances in cosmetics", *Ceska A Slovenska Farmacie*, 44(2):90–94, 1995

Hutchison, K. G., "Encapsulation for toiletries and cosmetics", *Seifen, Oele, Fette, Wachse* (Germany), 119:410, 412, 413, 1993

Tadros, T. F., "Future developments in cosmetic formulations", *International Journal of Cosmetic Science* (England), 14(3):93–111, 1992

Hughson, L., "Skin care the liposome way", *Pharmaceutical and Cosmetic Review* (South Africa), 19(Jul–Aug):17–18, 1992

Lautenschlager, H., "Liposomes in dermatological preparations. Part 2", *Cosmetics & Toiletries* (USA), 105(Jul):63–72, 1990

Suzuki, K. et al., "Application of liposomes to cosmetics", *Cosmetics & Toiletries* (USA) 105(May):65–78, 1990

Optional Skin Benefit Materials and Cosmetic Adjuncts

Skin Benefit Materials

Various types of additional active ingredients may be present in the cosmetic compositions of the present invention. The additional active ingredients are defined as skin benefit agents other than the active vitamin A derivative(s), and other than ingredients that merely improve the physical characteristics of the composition. Although not limited to this category, general examples include sunscreens and tanning agents.

Sunscreens include those materials commonly employed to block ultraviolet light. Illustrative compounds are the derivatives of PABA, cinnamate, salicylate and avobenzone. For example, octyl methoxycinnamate and 2-hydroxy-4- methoxy benzophenone (also known as oxybenzone) can be used. Octyl methoxycinnamate and 2-hydroxy-4-methoxy benzophenone are commercially available under the trademarks, Parsol MCX, Parsol 1789 and Benzophenone-3, respectively. Nonlimiting examples of tanning agents include melanin, lipomelanin, hydrolized collagen, DHA and acetyl etyrosine.

The amount of sunscreen and/or tanning agent employed in the compositions of the invention can vary depending upon the degree of protection desired from the sun's UV radiation. The concentration of such agents to be used in cosmetic formulations is well established in the art.

Functional Cosmetic Adjusts

Emollients are often incorporated into cosmetic compositions of the present invention. Emollients help to dissolve and/or disperse the active agent. If incorporated, levels of such emollients may range from at least about 0.5% to at least about 50%, preferably between at least about 5% and at least about 30% by weight of the total composition. Such emollients are added to the composition in addition to those incorporated with the vitamin A derivative prior to liposome formulation. Emollients may be classified under such general chemical categories as esters, fatty acids and alcohols, polyols and hydrocarbons.

Esters may be mono- or di-esters. Acceptable non-limiting examples of fatty di-esters include dibutyl adipate, diethyl sebacate, diisopropyl dimerate, and dioctyl succinate. Acceptable branched chain fatty esters include but are not limited to 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of coco-caprylate and coco-caprate), propylene glycol myristyl ether acetate, diisopropyl adipate and cetyl octanoate.

Suitable fatty alcohols and acids include, but are not limited to, those compounds having from 10 to 20 carbon atoms. Especially preferred are such compounds such as cetyl, myristyl, palmitic and stearyl alcohols and acids.

Among the non-limiting examples of polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Non-limiting exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the resent invention are thickeners. If present, a thickener will usually be present in amounts anywhere from at least about 0.1 to at least about 20% by weight, preferably from at least about 0.5% to at least about 10% by weight of the composition. Non-limiting exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening unction may be accomplished by a material also serving as a silicone or emollient. For instance, silicone gums in excess of 10 centistokes and esters such as glycerol stearate have dual functionality.

Powders may be incorporated into the cosmetic composition of the invention. Non-limiting examples of these powders may include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from about 0.001% up to about 20% by weight of the composition.

Use of the Composition

The composition according to the invention is intended primarily as a product for topical application to human skin. Especially for the cosmetic or dermatological treatment of imperfections or complaints of the skin, including the scalp. The composition according to the invention is particularly useful as an agent for conditioning and smoothing the skin, and preventing or reducing the appearance of wrinkled or aged skin and can thus be formulated into a topical skin treatment formulation for use in cosmetic applications. The topical skin treatment formulation of the invention is thus useful in the removal of oxidants from the skin and in the dermatological treatment of the skin including, but not limited to, skin imperfections, dry skin, photodamaged skin, wrinkles, age spots, acne, skin lightening, psoriasis, and atopic dermatosis In use, a small quantity of the topical skin treatment composition of the invention, for example from 1 to 5 ml, is applied to exposed areas of the skin, from a suitable container or applicator and, if necessary, it is then spread over and/or rubbed into the skin using the hand or fingers or a suitable device.

The topical skin treatment composition of the invention contains at least about 0.05% to at least about 5.0% of vitamin A derivative in the final composition.

Product Form and Packaging

The topical skin treatment composition of the invention for use in cosmetic applications can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

Stabilization of Vitamin A Derivatives in Cationic Vesicles

Encapsulation of vitamin A derivative in the CAT-EZOMES™ liposomes has a pronounced positive effect upon the stability of vitamin A derivative.

The liposome vesicles containing vitamin A derivative as prepared according to the invention with high pressure, high shear processing improve the long-term stability of the vitamin A derivative under all storage conditions. The encapsulated vitamin A derivative of the invention is thus well suited for formulation into the topical cosmetic formulations of the invention due to their increased stability. In addition, due to its cationic nature, the liposome composition of the invention remains on the skin for a prolonged period, and the increased stabilization of the vitamin A derivative provides for a longer term of delivery for the normally unstable vitamin A derivative payload. Destabilizing conditions may include storage temperature ranges of from 4° C. to 100° C. and acidic or basic environments. The stability of the encapsulated vitamin A derivative of the invention was tested herein using HPLC analysis to determine breakdown of the vitamin A derivative following storage at 4° C., 25° C., 40° C. and 50° C. for one month. (See Examples 4–11 below.)

The encapsulated vitamin A derivatives of the invention are thus stabilized against degradation during storage and are preferred for use in cosmetic formulations.

The liposomes of the invention are also used for encapsulating other hydrophobic and hydrophilic substances (ie., a "load material"). Examples of such hydrophobic and hydrophilic materials include water, active agent, genetic material or a personal care element.

As used herein, "genetic material" is defined as genetic material, specifically DNA/RNA oligonucleotides, genes, gene fragments and the like, and combinations thereof.

As used herein, "personal care element" is defined as water, a skin active, a hair active and a fragrance.

As used herein, a "skin active" is defined as any agent which exerts an effect on the skin. Examples of such skin actives used to encapsulate into the liposomes of the invention include water, organic sunscreens, pesticides, fragrances, oils, moisturizers e.g. alpha bisabolol, self-tanning agents, vitamin A derivatives, alpha hydroxy acids, beta hydroxy acids, topical anaesthetics, non-steroidal and steroidal anti-inflammatories, botanical extracts, proteins e.g. enzymes, known irritants including capsicum and it's derivatives, and combinations of said skin actives thereof.

As used herein, a "hair active" is defined as any agent which exerts an effect on the hair. Examples of such hair actives used to encapsulate into the liposomes of the invention include water, organic sunscreens, fragrances, oils, moisturizers, conditioners, silicones e.g. cyclomethicones, dimethicones and dimethiconols, pesticides e.g. those used in the treatment of lice infestations, proteins e.g. enzymes, including those used in the treatment of lice infestations and combinations of hair skin actives thereof.

EXAMPLE 1

B-BDDP is dispersed in phosphate-buffered saline (PBS: 20 mM phosphate buffer (pH 7.2) containing 140 mM NaCl) by stirring at a temperature of 70° C. for 20 minutes. The dispersion is then subjected to high-sheer processing by passage through a microfluidizer (Microfluidics, Newton, Mass.) five times, occurring at an operating pressure of 10,000 psi and an operating temperature between 10° C. and 20° C. It should be noted that any materials) to be incorporated into the liposomes are added either at the initial mixing stage or immediately prior to high-shear processing. It should be noted that the above process is also applicable to the production of CATEZOMES™ liposomes using other A-ADDA's, including, S-SDDP and P-PDDP.

Figure 6:
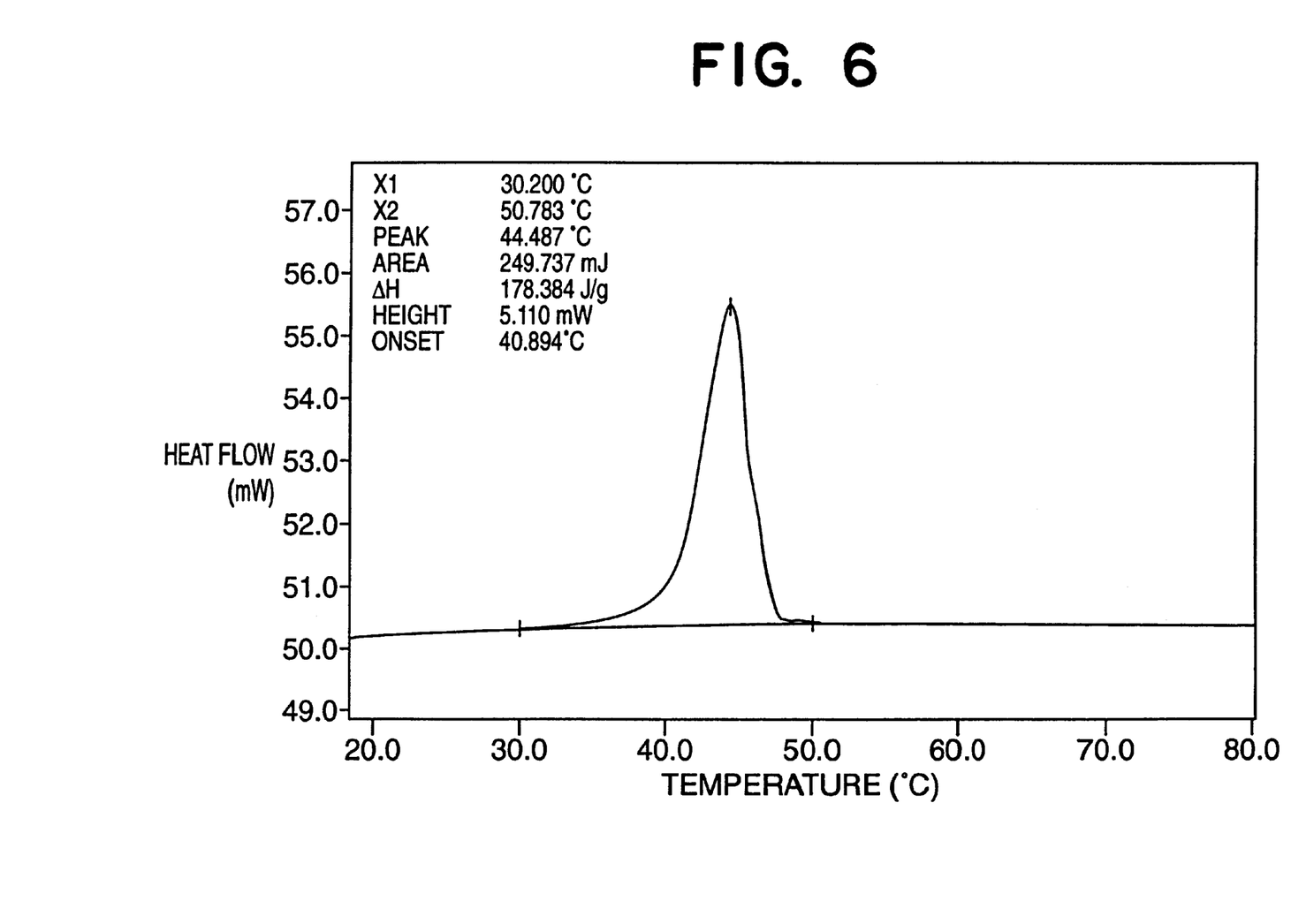
FIG. 6 is a differential scanning calorimetry plot (thermogram) of P-PDDP Liposomes prepared as described in the text.
Figure 7:
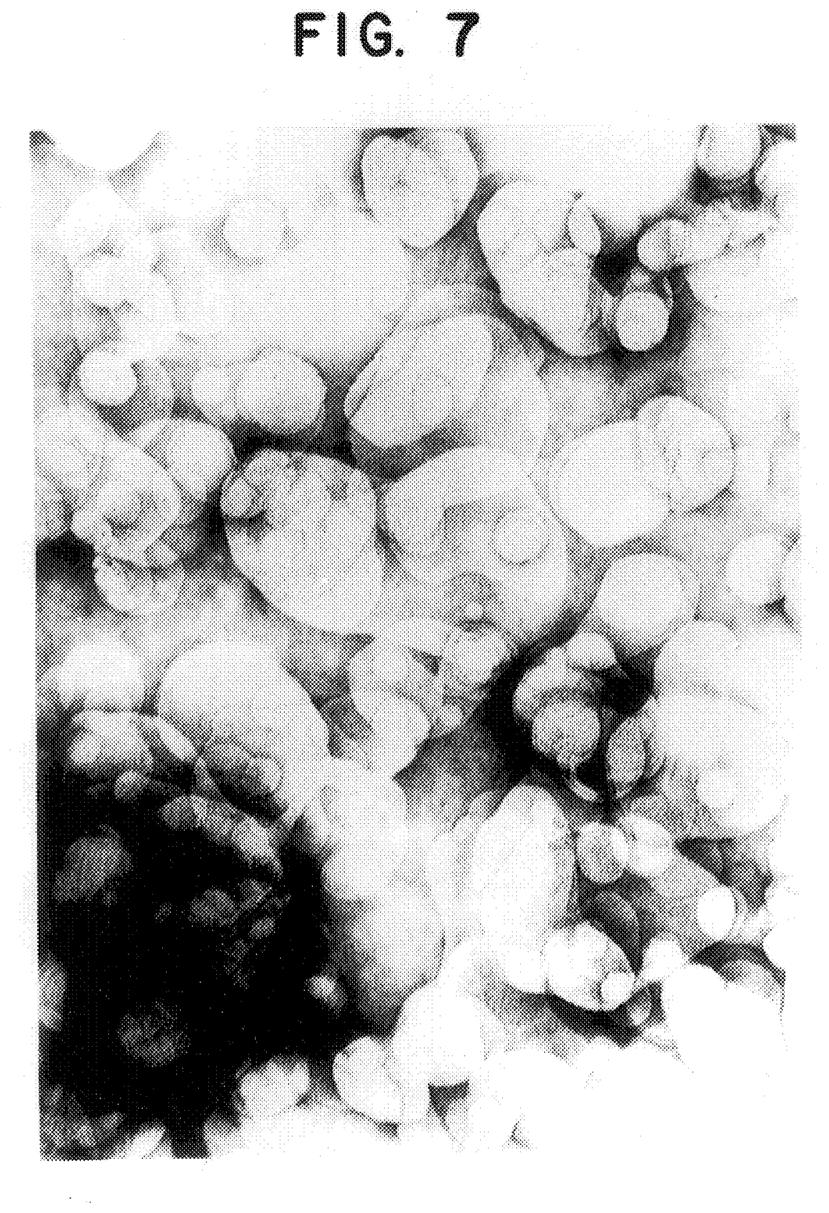
FIG. 7 is an image of a B-BDDP formed CATEZOMES™ liposomes by negative stain electron microscopy in accordance with the invention.

The integrity of the liposomes formed in accordance with Example 1 was affirmed using differential scanning calorimetry. The presence of a transition temperature characteristic of molecules in a liquid crystal arrangement, such as the alkyl chains of the liposome membranes, is shown in FIG. 6. Further demonstration of the formation of liposomes by B-BDDP is shown in a representative electron micrograph of FIG. 7.

The testing utilized to determine the payload efficiency of the CATEZOMES™ liposomes formed according to Example 1 is described in Example 2. In Example 2, Glucose was chosen as a model substance to examine the encapsulation capabilities of the subject liposomes because it is a low-molecular weight (180 g/mole), water-soluble, non-charged molecule. These characteristics make for the most difficulty in encapsulation for the following reasons. The low molecular weight means that even small, transient imperfections in the lipid membrane would permit leakage of the glucose from the vesicular space to the extra-vesicular space and thus the glucose will rapidly leave any but the most perfect liposomes. The fact that glucose is entirely water-soluble, lipid-insoluble means that there is no chance of the glucose partitioning into the lipid phase and therefore no "false encapsulation" will be apparent. Since the ADDAs have a positive charge due to the amine group, a negatively charged molecule would tend to be attracted to the membranes. Again this would be apparent as false encapsulation. Thus, although glucose is very difficult to encapsulate in liposomes, it constitutes the perfect test material to prove the existence of stable, flawless, enclosed vesicles.

EXAMPLE 2

Glucose was added to a Catemol 22OB/buffer dispersion at a concentration of 10% w/w and then the CATEZOMES™ liposomes were formed as described above in Example 1. Non-encapsulated, i.e., extra-vesicular, glucose was then removed by placing the liposomes into a dialysis bag (molecular weight cut-off 5,000 daltons), placing the dialysis bag into a beaker of PBS (phosphate-buffered saline) and then replacing the PBS with freshly made PBS every two hours for a twenty-four hour period. The concentration of glucose in the extravesicular volume (unencapsulated glucose) was measured by assaying the glucose in a liposome suspension in the presence or absence of 10% (v/v) Octoxynol-9 detergent manufactured by Union Carbide Corporation, of Danbury Connecticut. Octoxynol-9 is a non-ionic detergent which disrupts the liposomes and permits the equilibration of glucose between intra- and extra-vesicular spaces. An assay kit, purchased from Sigma Chemical Company of St. Louis, Mo. (product number 115), was used according to the manufacturer's instructions. This assay is based on the, enzymatic conversion of glucose to glucose-6-phosphate with the concomitant reduction of nicotinamide dinucleotide phosphate (NADP) which can be detected spectrophotometrically. The absorption ($520 \mu m$) of the test sample is then extrapolated by comparison to a linear progression of standard (known) concentrations of glucose. Statistical analysis results of the slopes of these standard curves in the absence or presence of octoxynol-9 is presented in Table 1. These results assured that no interference from the detergent was apparent.

TABLE 1

| Statistical Analysis of Glucose Standard Curves | | |
|---|---|---|
| [Octoxynol-9] | 0% | 10% |
| n | 32 | 28 |
| Mean Slope | 0.249 | 0.262 |
| Standard Deviation | 0.020 | 0.036 |

The concentration of glucose in the intravesicular volume (encapsulated glucose) is then determined by subtraction of the extra-vesicular glucose (measured in the absence of octyoxynol-9) from the total glucose (measured in the presence of octoxynol-9) (Equation 1).

$$[\text{Glucose}]_{inside} = [\text{Glucose}]_{total} - [\text{Glucose}]_{outside} \quad \text{Equation 1.}$$

In studies of liposomal encapsulation and stability, it is common to refer to "latency" which is the concentration of encapsulated payload expressed as a percentage of the total payload (Equation 2).

$$\text{Latency} = [\text{Glucose}]_{inside} \div [\text{Glucose}]_{total} \times 100 \quad \text{Equation 2 .}$$

The concentration of intravesicular glucose is defined interchangeably herein, either in terms of concentration (mg/ml) or latency as defined above.

The encapsulation ability of liposomes made in accordance hereto, which are referred to interchangeably herein by their trade name CATEZOMES™ from various A-ADDAs in various vehicles was also compared. All the CATEZOMES™ liposomes were formed in accordance with Example 1 above-described. For comparison, "standard" or conventional liposomes, i.e., those made from a phospholipid,(DPPC),1,2-dipalmitoyl-sn-glycero-3-phosphocholine were also tested. The resulting data are summarized in Table 2. It is clear that no matter the chain length, all of the A-ADDAs formed as in Example 1 were shown to form sealed liposomes which encapsulated varying amounts of glucose. Furthermore, the process was clearly shown by the resulting data to be independent of the buffer system being used.

TABLE 2

Glucose Encapsulation by Liposomes of Various Composition
(Valued are in [Glc]in, mg/mL)

| Buffer | B-BDDP | S-SDDP | P-PDDP | DPPC |
|---|---|---|---|---|
| Tris-buffered Saline | 0.5 | 1.5 | ND | ND |
| Phosphate-Buffered Saline | 0.3 | 4.1 | 1.7 | 1.0 |
| Water | 0.3 | 3.9 | 1.9 | 1.0 |

Figure 8:
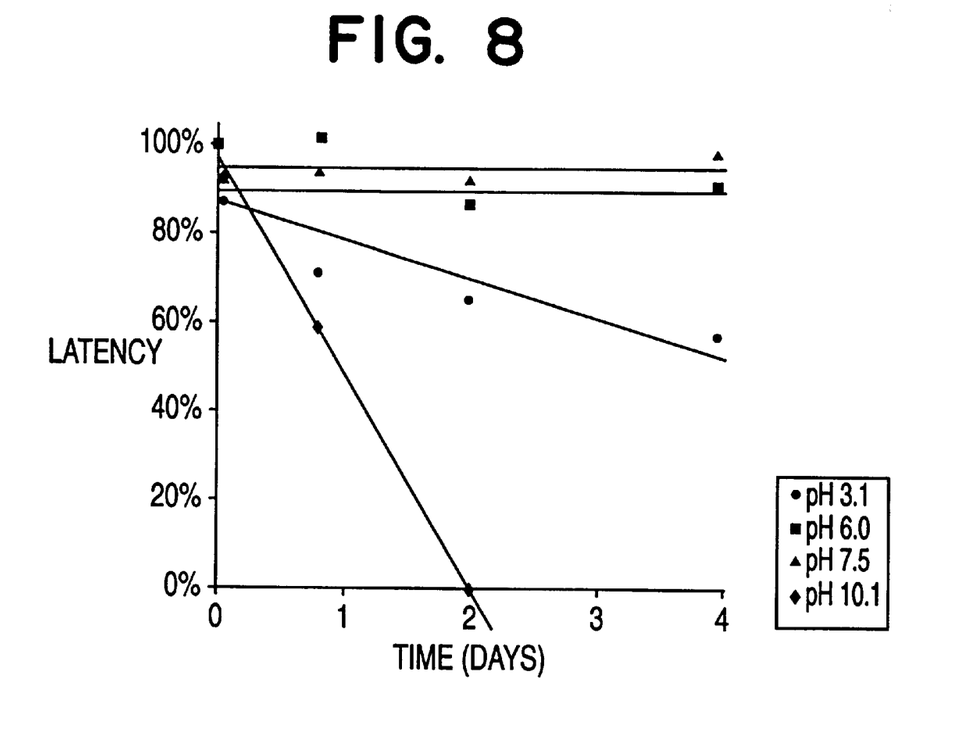
FIG. 8 is a plot of latency of a B-BDDP CATEZOMES™ liposomes formed in accordance herein.

B-BDDP, behenyl-$N_1$-behenamido-$N_2,N_2$-dimethyl-propyl-1,3-diamine [$CH_3(CH_2)_{20}COO.CH_3(CH_2)_{20}CONHCH_2CH_2CH_2N(CH_3)_2$]
S-SDDP, stearoyl-$N_1$stearoylamido-$N_2,N_2$-dimethyl-propyl-1,3-diamine [$CH_3(CH_2)_{16}COO.CH_3(CH_2)_{16}CONHCH_2CH_2CH_2N(CH_3)_2$]
P-PDDP, palmitoyl-$N_1$-palmitoylamido-$N_2,N_2$-dimethyl-propyl-1,3-diamine [$CH_3(CH_2)_{14}COO.CH_3(CH_2)_{14}CONHCH_2CH_2CH_2N(CH_3)_2$]
DPPC, 1,2-dipalmitoyl-sn-glycero-3-phosphocholine; Tris-Buffered Saline, 20 mM Tris HCl, pH 7.2, 140 mM NaCl; Phosphate-Buffered Saline, 20 mM phosphate, pH 7.2,140 mM NaCl;
ND - not determined As mentioned above, the molecular shape of the A-ADDAS, which precipitates bilayer and liposome formation, is in part dependent on the salt bridge comprising the molecule. Concomitantly, the stability of the liposomes is dependent upon changing pH and/or ionic strength, which acutely affects the salt bridge. FIG. 8 shows the latency over time of B-BDDP liposomes prepared in buffers of various pH but identical ionic strength. The B-BDDP liposomes containing glucose were prepared as described above (Example 1.) Samples of these liposomes were then placed into phosphate buffers of various pH as shown, but with constant ionic strength. The latency (Equation 2) of the liposomes was then measured, as described in the text, at various times following the onset of the experiment.

Figure 9:
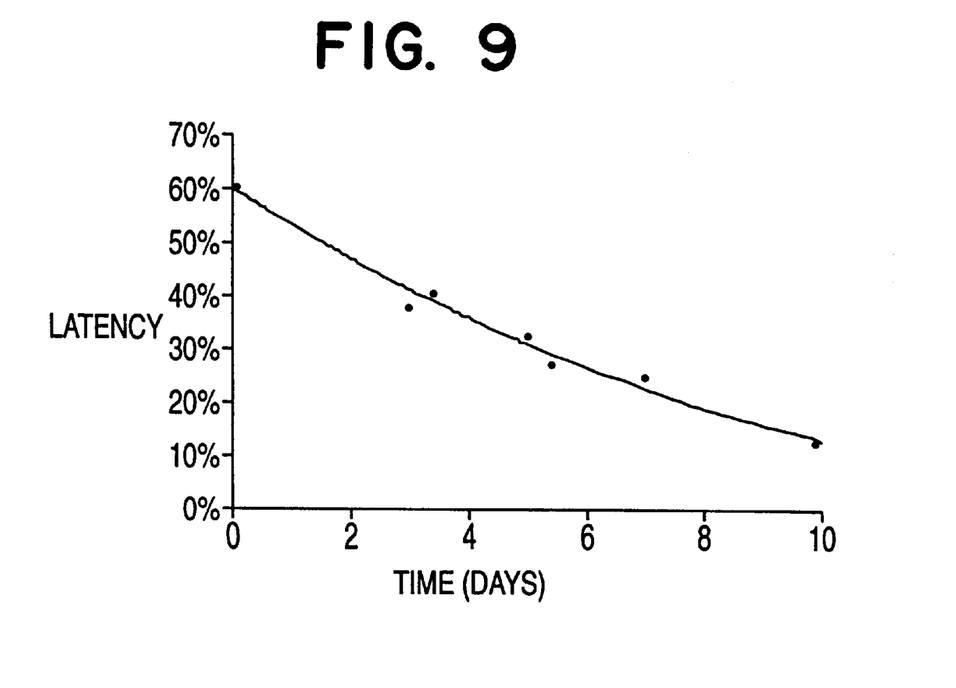
FIG. 9 is a plot of latency of a B-BDDP CATEZOMES™ liposomes containing glucose.

The measurement results clearly establish that the CATEZOMES™ liposomes are very stable at pH around neutrality, but become permeable to low molecular weight molecules such as glucose when the pH falls below 3 or increases above 10. This is entirely consistent with the notion that the salt bridge stabilizing the molecules is disruptable by pH. FIG. 9 shows the effect of increasing the ionic strength of the medium surrounding the CATEZOMES™ liposomes to 1.4 M NaCl. Clearly, the increased ionic strength disrupts the molecular structure of the B-BDDP and causes the liposomes to become permeable.

The experiments presented for B-BDDP in FIG. 8 and FIG. 9 were repeated for several other A-ADDAs and the data are presented in Table 3.

TABLE 3

Effects of pH and Ionic Strength on the Half-Life of A-ADDA Liposomes

|  | pH3 | pH10 | pH7 | Hypertonic |
|---|---|---|---|---|
| B-BDDP | <3 days | <1 day | >1 month | <1 day |
| S-SDDP | <1 day | <1 day | >1 month | <1 day |
| P-PDDP | <1 day | <3 days | >1 month | <1 day |
| DPPC | 3 days | >1 month | >1 year | >1 year |

B-BDDP, behenyl-$N_1$-behenamido-$N_2,N_2$-dimethyl-propyl-1,3-diamine [$CH_3(CH_2)_{20}COO.CH_3(CH_2)_{20}CONHCH_2CH_2CH_2N(CH_3)_2$]
S-SDDP, stearoyl-$N_1$-stearoylamido-$N_2,N_2$-dimethyl-propyl-1,3-diamine [$CH_3(CH_2)_{16}COO.CH_3(CH_2)_{16}CONHCH_2CH_2CH_2N(CH_3)_2$]
P-PDDP, palmitoyl-$N_1$-palmitoylamido-$N_2,N_2$-dimethyl-propyl-1,3-diamine [$CH_3(CH_2)_{14}COO.CH_3(CH_2)_{14}CONHCH_2CH_2CH_2N(CH_3)_2$]
DPPC, 1,2-dipalmitoyl-sn-glycero-3-phosphocholine

EXAMPLE 3

BDDP and a less than equimolar amount of Behenyl acid is dispersed in PBS along with lysozyme. The resulting CATEZOMES™ liposomes were found to display a cationic nature, and upon testing, found to bind readily to hair shafts and chitin shells of nits (eggs of head lice). Once the CATEZOMES™ liposomes are bound, surface interactions realize environmental characteristic changes, e.g., the result of the excretion of salts and/or acids by the skin or hair which cause payload release to begin and the lysozyme contacts and destroys the egg shell. Similarly, CATEZOMES™ liposomes formed in accordance hereto as containers for silicones were found to readily adhere to hair shafts for conditional delivery.

The following examples are intended as non-limiting illustration of the present invention.

EXAMPLES 4–11

Stabilization of Vitamin A Derivative

Summary of Methods

The stability of retinol, both in solution and in cationic vesicles, was examined under a variety of storage conditions over a period of thirty days. Samples of retinol dissolved at 10% w/w in soy oil and 10% w/w in caprylic/capric triglycerides, respectively, were used as controls. Aqueous cationic vesicles of these solutions were prepared with an 80:20 ratio of aqueous to organic phases. Aliquots of all samples were stored in clear borosilicate glass screw top jars at 4° C., 25° C., 40° C., and 50° C. to study the effect of temperature on stability Analysis of the samples was carried out using reversed phase HPLC with photodiode array detection. Encapsulation had a significant positive effect upon the stability of retinol under all conditions studied. Specific materials and methods as well as experimental data are described below and in Examples 4–11 below.

Materials and Reagents

Solvents and other reagents utilized include methanol, HPLC grade (EM Science, Location), acetonitrile, HPLC grade (EM Science, Location), phosphoric acid, 85% ACS reagent grade (Spectrum, Location). Samples of retinol in soy oil, 10% w/w (Retinol 10S) and retinol in capric caprylic triglycerides 10% w/w (Retinol CM) were obtained from BASF (Mount Olive, N.J.).

Reagents used to prepare the cationic vesicles were as follows: B-BDDP (Phoenix Chemical, Somerville, N.J.), Carbowax Sentry PEG 200 (Union Carbide Chemicals and Plastics Co., Danbury, Conn.), Germazide MPB (Collaborative Laboratories, East Setauket, N.Y.), and deionized water (DI water). Methods and materials used for the preparation of the cationic vesicles of the invention are disclosed below and in the above-identified U.S. Pat. No. 5,874,105, which has been incorporated herein by reference in its entirety.

The HPLC system used consisted of a Waters model 600E pump, a model 717 autosampler, a model CHM column heater module, and a model 991 M photodiode array detector (Waters Corp., Milford, Mass.). The chromatography data management software was Waters Millennium, version 2.10. The HPLC column used was a reversed phase 250 mm×4.6 mm Inertsil C8 column with a 5.0 $\mu$M particle size and a 100 Å pore size. (Metachern Technologies, Inc., Torrance, Calif.). Incubators with temperatures set at 4° C., 25° C., 40° C., and 50° C. were used to store samples for thermal degradation studies.

Analytical Sample Preparation 5.0 mL aliquots of both of the 10% retinol solutions were placed into separate 1.0-oz glass jars with screw top lids. 5.0 mL aliquots of the vesicles made from the 10% retinol solutions were stored similarly. Once aliquoted, samples for the thermal stability studies were placed in 4° C., 25° C., 40° C., and 50° C. incubators. In preparation for analysis, samples were diluted in neat methanol to contain 40 to 110 $\mu$g of retinol per niL, filtered through 0.45 $\mu$M nylon syringe filters, and injected at a 10.0 $\mu$L each.

System Stability Sample Preparation

A solution of methyl-p-hydroxybenzoate at 25.3 mg in 200 mL of neat methanol was prepared in order to monitor HPLC system stability over the course of the experiment. This compound was chosen due to its stability in methanolic solution and it's compatibility with the analytical methodology employed.

HPLC Analysis

The HPLC mobile phase consisted of a binary gradient of aqueous 0.1% $H_3PO_4$(A) and neat acetonitrile (B) run according to Table 4 below. The injection volume for all samples was 10.0 $\mu$l, and the column temperature was set at 35° C. The photodiode array detector was set to acquire data between 210 and 400 nm with a resolution of 2.6 nm at a rate of 1.0 spectrum per second. The analytical wavelength for retinol was 324 nm and the analytical wavelength for methyl-p-hydroxybenzoate was 254 nm.

TABLE 4

HPLC Gradient

| Time (min) | Flow Rate (mL/min) | % aq. 0.1% Phosphoric Acid | % Acetonitrile | Curve |
|---|---|---|---|---|
| 0.0 | 1.20 | 70 | 30 | NA |
| 17.0 | 1.20 | 19 | 81 | 4 (concave) |
| 25.0 | 1.20 | 0 | 100 | 7 (convex) |
| 45.0 | 1.20 | 70 | 30 | None |
| 70.0 | 0.0 | 70 | 30 | None |

HPLC System Stability 10.0 $\mu$L of the methanolic solution of methyl-p-hydroxybenzoate prepared above was injected at least once per data acquisition session to monitor the system response per unit mass injected. This was done because fresh samples of retinol were not available for use as external standards for this experiment. The peak area response per pg of methyl-p-hydroxybenzoate injected at each time point is shown in Table 5. According to the data shown in Table 5, the response of the HPLC system per unit mass of material injected was shown to be quite stable over time.

TABLE 5

| Elapsed Time | Response |
|---|---|
| 0 | 4339145 |
| 7 | 4292585 |
| 15 | 4460978 |
| 29 | 4321623 |
| Mean | 4353583 |
| Std Dev | 74127 |
| %RSD | 1.70 |

EXAMPLE 4

Preparation of Cationic Vesicles

| Ingredient | Percentage (w/w) |
|---|---|
| DI Water | 69.50% |
| 10% w/w Retinol 10S | 20.00% |
| Co-solvent (PEG200) | 7.00% |
| B-BDDP | 2.00% |
| Biocide (Germazide MPB) | 1.50% |

The above-listed ingredients were combined in a glass beaker, then the temperature was increased to approximately 80° C. (±5° C.) with a hot water bath. The samples were mixed with a 1.25 inch diameter stainless steel marine prop for approximately 30 minutes until homogeneous. Samples were then removed from the heat and processed with a total of five passes through the high pressure, high shear apparatus at between 10,000 PSI to 14,000 PSI. The final product was a viscous, opaque, yellow liquid. The pH of the Retinol 10S vesicles was measured to be 4.89. The average particle size for the liposomes made according to the Example ranged from approximately 150 nm to approximately 400 nm.

EXAMPLE 5

Preparation of Cationic Vesicles

| Ingredient | Percentage (w/w) |
|---|---|
| DI Water | 69.50% |
| 10% w/w Retinol CM | 20.00% |
| Co-solvent (PEG200) | 7.00% |
| B-BDDP | 2.00% |
| Biocide (Germazide MPB) | 1.50% |

The above-listed ingredients were combined and treated as in Example 1. The final product was a viscous, opaque, yellow liquid. The pH of the retinol CM vesicles was measured to be 4.57. The average particle size for the liposomes made according to the Example ranged from approximately 150 nm to approximately 400 nm.

EXAMPLE 6

Preparation of Cationic Vesicles

| Ingredient | Percentage (w/w) |
|---|---|
| DI Water | 76.50% |
| 10% w/w Retinol 10S | 20.00% |

-continued

| Ingredient | Percentage (w/w) |
|---|---|
| B-BDDP | 2.00% |
| Biocide (Germazide MPB) | 1.50% |

The above-listed ingredients were combined and treated as in Example 1. The final product was a viscous, opaque, yellow liquid. The pH of the vesicles was measured to be 4.6. The average particle size for the liposomes made according to the Example ranged from approximately 150 nm to approximately 400 nm.

EXAMPLE 7
Retinol Remains Unchanged When Encapsulated in Cationic Vesicles

Figure 10:
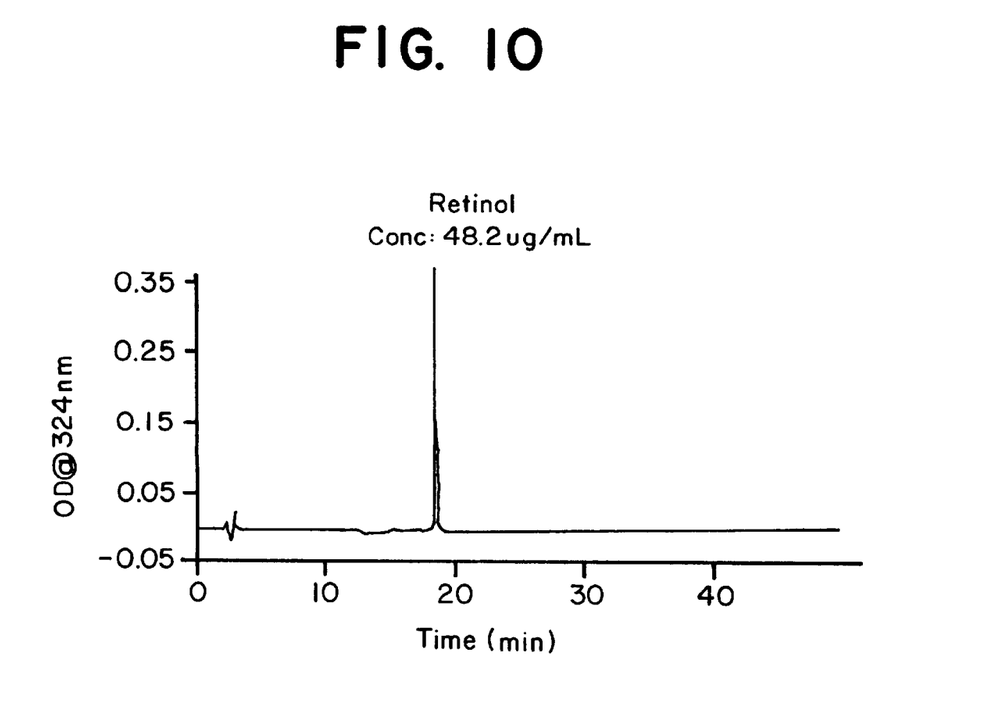
FIG. 10 is a chromatogram at 324 nm of a freshly prepared sample of retinol in soy oil (T0).

FIG. 10 shows a chromatogram at 324 nm of a freshly prepared sample of retinol in soy oil (TO). The fresh (TO) samples of retinol in capric/caprylic triglycerides and both of the encapsulated retinol samples of Examples 4 and 5 yielded identically appearing separations to the one shown. (Data not shown.) The retinol peak at 18.8±0.3 min appeared to be spectrally pure in all samples assayed.

Samples collected as described above were analyzed with HPLC to determine degradation of retinol when stored over time at various temperatures. The data are provided in Examples 8–11 below.

EXAMPLE 8
Degradation of Retinol at 4° C.

Figure 11:
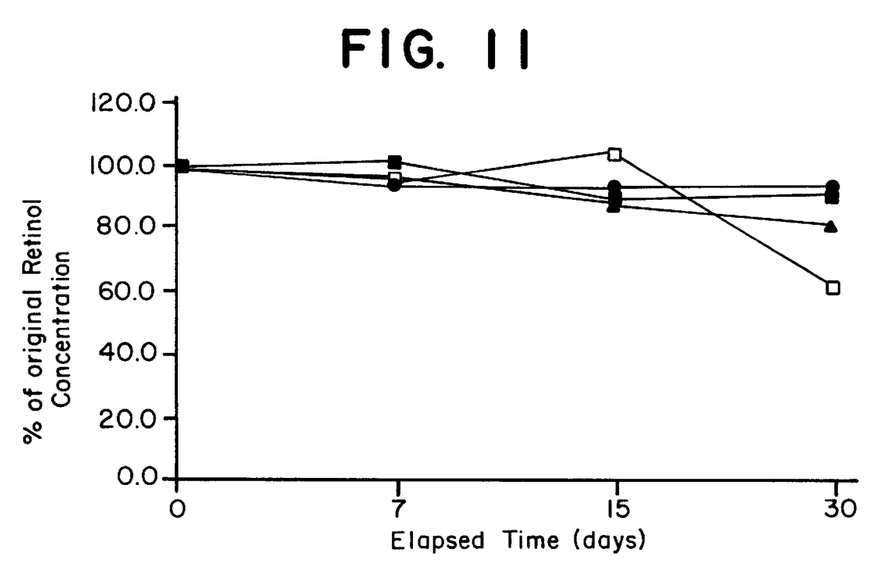
FIG. 11 is a graph showing the degradation of retinol during storage at 4° C. for retinol 10S in Catezomes™ (—♦—), retinol 10S alone (—▲—), retinol 10CM in Catezomes™ (—■—), and retinol 10CM alone (—x—).

FIG. 11 and Table 6 show the degradation of retinol which occurred during storage at 4° C. The degradation rate appears to be slow at this temperature and a significant improvement in stability is seen at T=30 days.

TABLE 6

| ET Days | Retinol 10S Catezomes | Retinol 10 CM Catezomes | Retinol 10S | Retinol 10CM |
|---|---|---|---|---|
| 0 | 100 | 100.0 | 100.0 | 100.0 |
| 7 | 93.8 | 100.8 | 95.7 | 95.0 |
| 15 | 92.9 | 89.4 | 88.0 | 104.0 |
| 30 | 93.5 | 91.3 | 81.4 | 61.2 |

EXAMPLE 9
Degradation of Retinol at 25° C.

Figure 12:
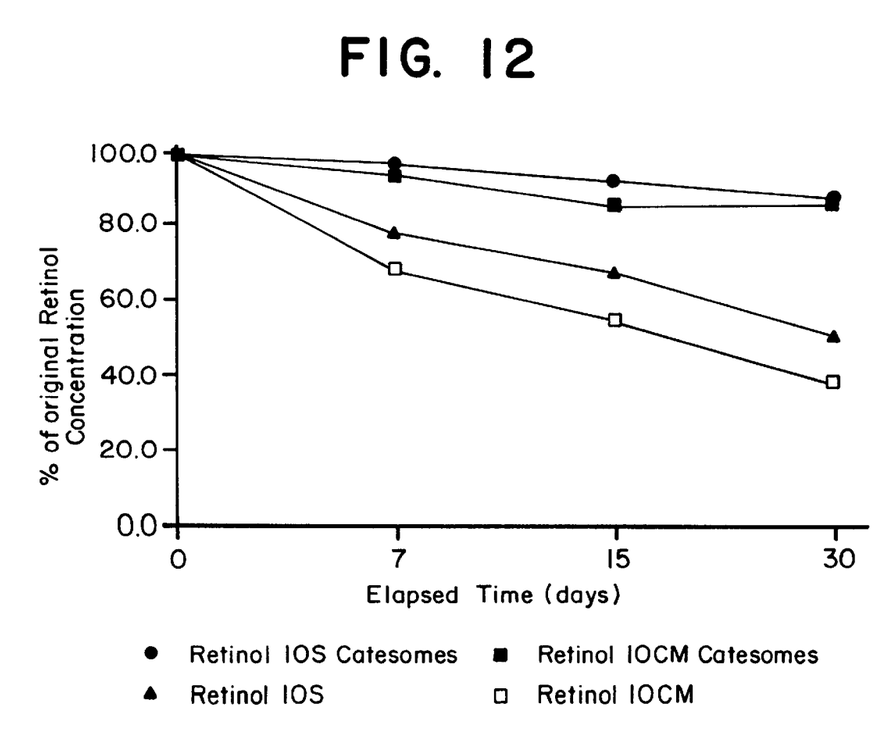
FIG. 12 is a graph showing the degradation of retinol during storage at 25° C. for retinol lOS in Catezomes™ (—♦—), retinol 10S alone (—▲—), retinol 10CM in Catezomes™ (—■—), and retinol 10CM alone (—x—).

FIG. 12 and Table 7 show the degradation of retinol which occurred during storage at 25° C. The degradation rate of the retinol in solution is significantly higher than the degradation rate in the vesicles. Further, the difference in stability of retinol between the two solutions is beginning to become apparent at this temperature.

TABLE 7

| ET | Retinol 10S Catezomes | Retinol 10CM Catezomes | Retinol 10S | Retinol 10CM |
|---|---|---|---|---|
| 0 | 100.0 | 100.0 | 100.0 | 100.0 |
| 7 | 97.2 | 94.9 | 78.3 | 68.6 |
| 15 | 93.5 | 86.8 | 68.2 | 55.2 |
| 30 | 88.5 | 87.7 | 51.6 | 39.4 |

EXAMPLE 10
Degradation of Retinol at 40° C.

Figure 13:
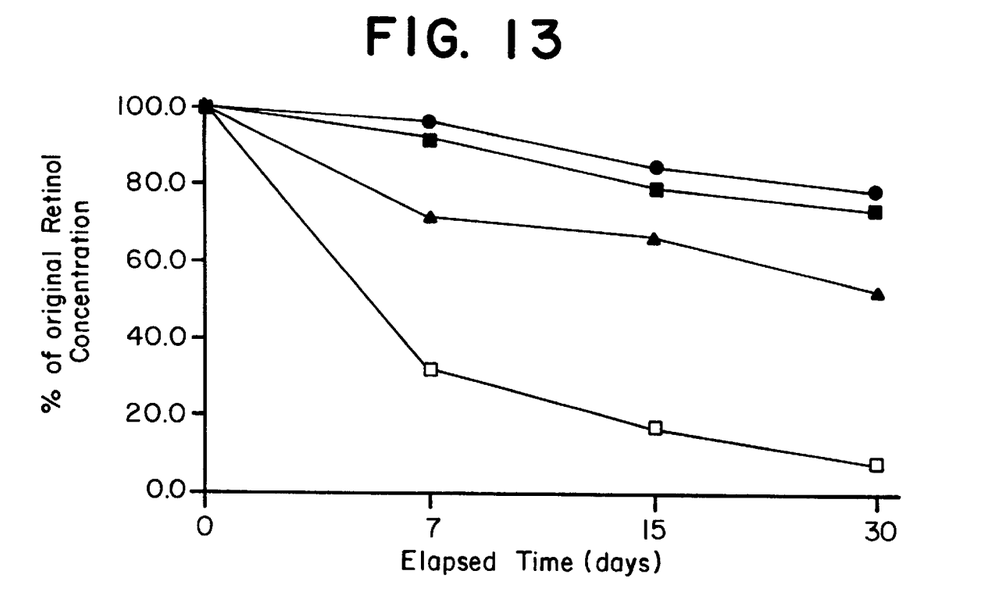
FIG. 13 is a graph showing the degradation of retinol during storage at 40° C. for retinol 10S in Catezomes™ (—♦—), retinol 10S alone (—▲—), retinol 10CM in Catezomes™ (—■—), and retinol 10CM alone (—x—).

FIG. 13 and Table 8 show the degradation of retinol which occurred during storage at 40° C. The degradation rate of the retinol in solution is much higher than the degradation rate in the vesicles at this temperature. The difference in stability of retinol between the soy oil and caprylic/capric triglycerides solutions is also significant.

TABLE 8

| ET | Retinol 10S Catezomes | Retinol 10CM Catezomes | Retinol 10S | Retinol 10CM |
|---|---|---|---|---|
| 0 | 100.0 | 100.0 | 100.0 | 100.0 |
| 7 | 92.6 | 93.2 | 70.3 | 41.5 |
| 15 | 82.5 | 81.5 | 59.3 | 26.9 |
| 30 | 78.5 | 76.6 | 45.7 | 13.7 |

EXAMPLE 11
Degradation of Retinol at 50° C.

Figure 14:
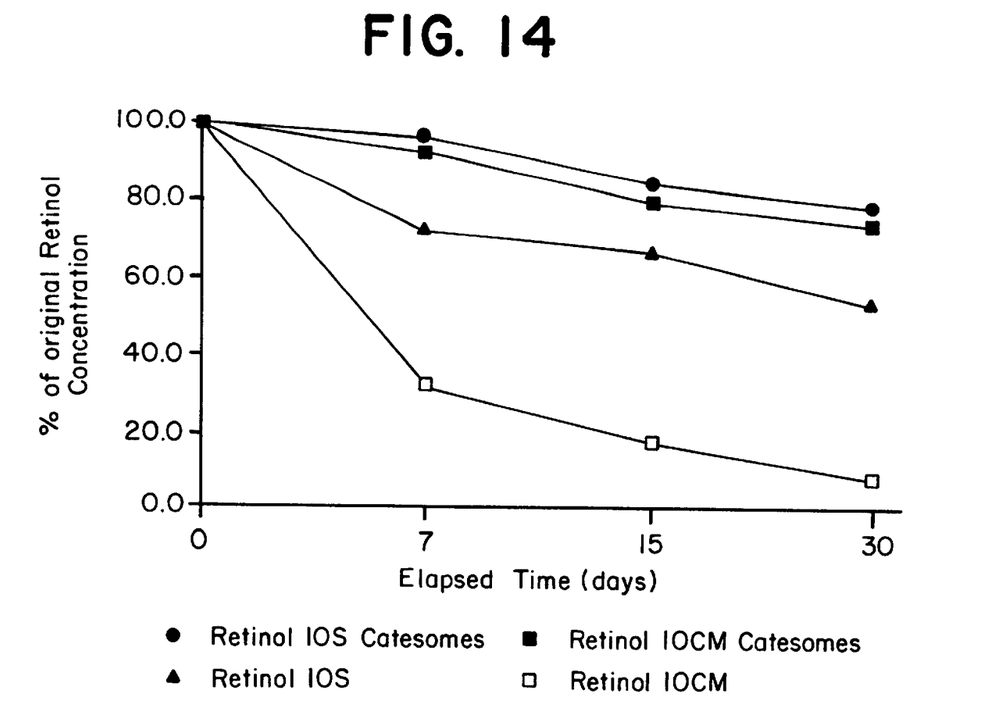
FIG. 14 is a graph showing the degradation of retinol during storage at 50° C. for retinol 10S in Catezomes™ (—♦—), retinol 10S alone (—▲—), retinol 10CM in Catezomes™ (—■—), and retinol 10CM alone (—x—).

FIG. 14 and Table 9 show that after 30 days at 50° C., nearly 100% of the retinol in caprylic/capric triglycerides (Retinol 10CM) and nearly 50% of the retinol in soy oil (Retinol 10S) had been degraded, whereas approximately 75% of the retinol in each of the encapsulated samples of Examples 4 and 5 remains intact.

TABLE 9

| ET | Retinol 10S Catezomes | Retinol 10CM Catezomes | Retinol 10S | Retinol 10CM |
|---|---|---|---|---|
| 0 | 100.0 | 100.0 | 100.0 | 100.0 |
| 7 | 96.6 | 92.4 | 72.3 | 110 |
| 15 | 84.4 | 79.6 | 67.0 | 17.4 |
| 30 | 78.3 | 73.7 | 53.5 | 8.4 |

As shown in Examples 4–11, encapsulation of the vitamin A derivative retinol in the cationic liposone vesicles of the invention had a pronounced positive effect upon the stability of retinol under all conditions studied. The encapsulated samples of retinol in the soy oil emollient showed the greatest stability over the thirty day period, followed closely by the encapsulated retinol in the capric caprylic triglycerides emollient (Retinol 10S Catezomes and Retinol CM Catezomes, respectively).

What has been described herein is merely descriptive of the preferred embodiments of this invention. It is not meant in any way to limit the scope and spirt of this invention, which is only to be limited by the following claims drawn in accordance with U.S. patent law.

What is claimed is:

1. A liposome composition comprising alkylammonium fatty acid salts and a vitamin A derivative selected from the group consisting of retinol, retinyl ester and any combination thereof, wherein said liposome composition is substantive to epithelial cells and skin, said liposome formed by a process comprising the steps of:
    (a) dispersing long chain acyl $N_n,N_n$-dimethyl-1,n-diamino alkyl (A-ADDA) molecules and said vitamin A derivative in a buffering solution to form a dispersion, said buffering solution having a pH within a range of between about 3.0 to around 10.0 and an ionic strength less than or equivalent to 1 molar NaCl; and
    (b) subjecting the dispersion to high shear processing.

2. The liposome of claim 1, wherein said vitamin A derivative is added to said buffering solution before said A-ADDA is added.

3. The liposome of claim 1, wherein said vitamin A derivative is added to said buffering solution after said A-ADDA is added.

4. The liposome of claim 1, wherein said buffer solution comprises $H_2O$ and the alkylammonium fatty acid salt is trialkylammonium fatty acid salt.

5. The liposome of claim 1, wherein said step of dispersing comprises dispersing with a mechanical homogenizer.

6. The liposome of claim 1, wherein said step of dispersing is conducted at a temperature above that of the melting point of said A-ADDA.

7. The liposome of claim 1, wherein said buffering solution has a pH of between about 5.5 and 10.5 and an ionic strength of less than the equivalent of 1 molar NaCl.

8. The liposome of claim 1, wherein the pH of said buffering solution is approximately 7.5.

9. The liposome of claim 1, wherein said A-ADDA is prepared from a molecule of ADDA and a fatty acid at a pH of between about 6 and 10.

10. A topical skin treatment formulation comprising a vitamin A derivative selected from the group consisting of retinol, retinyl ester or any combination thereof, said vitamin A derivative being encapsulated by a liposome, wherein said liposome comprises alkylammonium fatty acids salts and wherein said liposome is substantive to epithelial cells and skin, said encapsulation formed by a process comprising the steps of:

(a) dispersing long chain acyl $N_n,N_n$-dimethyl-1,n-diamino alkyl (A-ADDA) molecules and said vitamin A derivative in a buffering solution to form a dispersion, said buffering solution having a pH within a range of between about 3.0 to around 10.0 and an ionic strength less than or equivalent to 1 molar NaCl;

(b) subjecting the dispersion to high shear processing.

11. A method for the dermatological treatment of a skin condition, comprising applying a topical cosmetic skin formulation comprising a vitamin A derivative selected from the group consisting of retinol, retinyl ester or any combination thereof, said vitamin A derivative being encapsulated by a liposome, wherein said liposome comprises alkylammonium fatty acids salts and wherein said liposome is substantive to epithelial cells and skin, comprising the steps of:

(a) dispersing long chain acyl $N_n,N_n$-dimethyl-1,n-diamino alkyl (A-ADDA) molecules and said vitamin A derivative in a buffering solution to form a dispersion, said buffering solution having a pH within a range of between about 3.0 to around 10.0 and an ionic strength less than or equivalent to 1 molar NaCl;

(b) subjecting the dispersion to high shear processing;

(c) isolating the liposome encapsulated vitamin A derivative product;

(d) incorporating said product into a topical skin treatment formulation; and (e) applying said topical skin treatment formulation to the skin.

12. A method according to claim 11, wherein said skin condition is selected from the group consisting of imperfections, dry skin, photodamaged skin, wrinkles, age spots, acne, skin lightening, psoriasis, and atopic dermatosis.

13. A method of stabilizing a vitamin A derivative comprising encapsulating said derivative in a liposome, wherein said liposome comprises alkylammonium fatty acids salts, said encapsulation formed by a process comprising the steps of:

(a) dispersing long chain acyl $N_n,N_n$-dimethyl-1,n-diamino alkyl (A-ADDA) molecules and said vitamin A derivative in a buffering solution to form a dispersion, said buffering solution having a pH within a range of between about 3.0 to around 10.0 and an ionic strength less than or equivalent to 1 molar NaCl;

(b) subjecting the dispersion to high shear processing.

14. The method of claim 13, wherein said vitamin A derivative is added to said buffering solution before said A-ADDA is added.

15. The method of claim 13, wherein said vitamin A derivative is added to said buffering solution after said A-ADDA is added.

16. The method of claim 13, wherein said buffer solution comprises $H_2O$ and the alkylammonium fatty acid salt is trialkylammonium fatty acid salt.

17. The method of claim 13, wherein said step of dispersing comprises dispersing with a mechanical homogenizer.

18. The method of claim 13, wherein said step of dispersing is conducted at a temperature above that of the melting point of said A-ADDA.

19. The method of claim 13, wherein said buffering solution has a pH of between about 5.5 and 10.5 and an ionic strength of less than the equivalent of 1 molar NaCl.

20. The method of claim 13, wherein the pH of said buffering solution is approximately 7.5.

21. The method of claim 13, wherein said A-ADDA is prepared from a molecule of ADDA and a fatty acid at a pH of between about 6 and 10.

* * * * *